United States Patent [19]  [11] Patent Number: 4,556,665
Erhardt et al.  [45] Date of Patent: Dec. 3, 1985

[54] CARDIOTONIC 1,3-DIHYDRO-4-[[(IMIDAZOL-1-YL)ARYL]-CARBONYL]IMIDAZOL-2-ONES

[75] Inventors: Paul W. Erhardt, Long Valley; Alfred A. Hagedorn, III, Edison, both of N.J.; William C. Lumma, Jr., Pennsburg, Pa.; Ronald A. Wohl, Morris Plains, N.J.

[73] Assignee: Schering A.G., Berlin, Fed. Rep. of Germany

[21] Appl. No.: 628,875

[22] Filed: Jul. 9, 1984

[51] Int. Cl.[4] ............... A61K 31/415; A61K 31/44; C07D 233/70; C07D 401/14
[52] U.S. Cl. ..................... 514/338; 548/318; 546/271; 546/278; 514/341; 514/392
[58] Field of Search ............ 548/318; 546/271, 278; 424/263, 273 R; 514/338, 341, 392

[56] References Cited

U.S. PATENT DOCUMENTS 4,367,236 1/1983 Grisar et al. ............. 548/318
4,405,628 9/1983 Dage et al. ............. 424/263
4,405,635 9/1983 Schnettler et al. ......... 424/273 R
4,447,619 5/1984 Grisar et al. ............ 546/278

FOREIGN PATENT DOCUMENTS

EP0118790A1 2/1984 European Pat. Off. ........... 548/318

Primary Examiner—Richard A. Schwartz
Assistant Examiner—Kurt G. Briscoe
Attorney, Agent, or Firm—Elizabeth A. Bellamy; John L. White; I. William Millen

[57] ABSTRACT

Novel imidazolonecarbonylarylimidazoles of the formula:

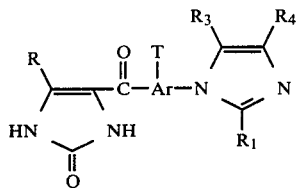

are described having cardiovascular properties, especially as cardiotonic agents in the treatment of congestive heart failure. Pharmaceutical formulations containing such compounds are also provided. Further, a novel process for the preparation of the compounds and intermediates useful thereto of this invention is disclosed.

19 Claims, No Drawings

CARDIOTONIC 1,3-DIHYDRO-4-[[(IMIDAZOL-1-YL)ARYL]CARBONYL]IMIDAZOL-2-ONES

PRIOR ART

The novel compounds described herein are potent cardiotonic agents. The closest prior art are the 4-aroyl-1,3-dihydro-2H-imidazol-2-ones described in U.S. Pat. No. 4,405,635 wherein the aroyl function is derivatized by pyrrolidino, piperidino, morpholino, piperazino and N-alkylpiperazino moieties, respectively. The aroyl function when derivatized by these cyclic aliphatic amino functions have much decreased cardiotonic activity as illustrated in J. Med. Chem. 1982, 25, 1477–1481.

FIELD OF THE INVENTION

This invention relates to novel imidazolonecarbonylarylimidazoles and their uses as cardiovascular agents. More specifically, this invention relates to (1,3-dihydro-2-oxo-1H-imidazole-4-carbonyl)aryl-1H-imidazoles and their pharmaceutically acceptable salts, to pharmaceutical compositions containing them as active ingredients and to the method of using them as cardiovascular agents, especially as cardiotonic agents in the treatment of congestive heart failure. This invention is also inclusive of a novel process for the preparation of certain of the compounds of this invention and intermediates thereto, some of which intermediates are known compounds with cardiotonic activity.

GENERAL DESCRIPTION OF THE INVENTION COMPOSITION-OF-MATTER ASPECT

In its composition-of-matter aspect this invention relates to novel imidazolonecarbonylarylimidazoles and their pharmaceutically acceptable salts. Particularly, this invention relates to the novel compounds defined by the following Formula I wherein
  R is hydrogen or loweralkyl;
  Ar is phenyl or pyridyl;
  T is hydrogen, hydroxy, halogen or loweralkyl;
  $R_1$, $R_3$ and $R_4$ are hydrogen or loweralkyl optionally substituted by 0 to 2 hydroxyl groups; or $R_3$ and $R_4$ taken together form a benzene ring;
with the provisos that:
  (a) when T is hydroxy, Ar is phenyl,
  (b) when one of $R_1$, $R_3$ and $R_4$ is loweralkyl substituted with 2 hydroxyl groups, both hydroxyls cannot be on the same carbon atom;
and the pharmaceutically acceptable salts thereof.

As used herein the term halogen represents fluorine, chlorine and bromine. The term loweralkyl represents a straight or branched chain alkyl of from one to six carbon atoms, as, for example, methyl, ethyl, isopropyl, tertiary butyl, n-pentyl, isopentyl, and 2,3-dimethylbutyl. The term loweralkyl group optionally substituted with zero to two hydroxyl groups is taken to mean a loweralkyl group as defined above bearing none, one or two hydroxyl groups at any available position with the provisos that if two hydroxyl groups are present they are not attached to the same carbon atom. Examples of such defined groups are hydroxymethyl, 2-hydroxyethyl, 2,3-dihydroxypropyl.

Among the compounds as defined in Formula I are sites for possible stereoisomerism, e.g. asymmetric carbon atoms. Any of the optical isomers thus possible are considered to be part of this invention.

Also contemplated as part of this invention are the pharmaceutically acceptable salts of the compounds of Formula I. Such salts may be of the base or acid addition variety. Among the base addition salts are those with a pharmaceutically acceptable metal ion such as sodium, potassium, calcium, zinc or aluminum. Acid addition salts may be formed with inorganic or organic acids. Illustrative but not restrictive examples of such acids include hydrochloric, hydrobromic, sulfuric, phosphoric, acetic, benzoic, methanesulfonic, and 2-hydroxyethanesulfonic acid. In general, these acid and base addition salts are crystalline solids exhibiting high melting points. In comparison to the parent compounds, these salts usually exhibit greater solubility in water and hydrophilic organic solvents.

Preferred classes of compounds embodied by this invention are those of the above general Formula I having one of the following characteristics:
  (a) Ar is phenyl,
  (b) R is loweralkyl,
  (c) T is hydrogen.

The more preferred compounds of this invention are those containing all the above (a), (b), and (c) characteristics.

The most preferred compounds of this invention are those of the following Formula II:

wherein
  R is loweralkyl; and
  $R_1$, $R_3$, and $R_4$ are as previously defined.

Most especially preferred within the compounds of Formula II are those wherein R is methyl or ethyl and $R_1$, $R_3$, and $R_4$ are hydrogen or loweralkyl with no hydroxyl substituents.

The compounds which follow are some of those which serve to exemplify the various composition-of-matter and/or process aspects of the invention described herein.
  (a) 1,3-Dihydro-4-methyl-5-[4-(2-methyl-1H-imidazol-1-yl)benzoyl]-2H-imidazole-2-one,
  (b) 1,3-Dihydro-4-[[2-(1H-imidazol-1-yl)pyridin-4-yl]carbonyl]-5-methyl-2H-imidazol-2-one,
  (c) 1,3-Dihydro-4-[4-(1H-imidazol-2-yl)benzoyl]-5-methyl-2H-imidazol-2-one,
  (d) 4-[4-(1H-Benzimidazol-1-yl)benzoyl]-1,3-dihydro-5-methyl-2H-imidazol-2-one,
  (e) 1,3-Dihydro-4-[4-(2-hydroxymethyl-1H-imidazol-1-yl)benzoyl]-5-methyl-2H-imidazol-2-one, (f) 1,3-Dihydro-4-[4-(1H-imidazol-1-yl)benzoyl]-5-methyl-2H-imidazol-2-one,
(g) 1,3-Dihydro-4-methyl-5-[4-(4-methyl-1H-imidazol-1-yl)benzoyl]-2H-imidazol-2-one,
(h) 1,3-Dihydro-4-methyl-5-[4-(2,4,5-trimethyl-1H-imidazol-1-yl)benzoyl]-2H-imidazol-2-one,
(i) 4-Ethyl-1,3-dihydro-5-[4-(2-methyl-1H-imidazol-1-yl)benzoyl]-2H-imidazol-2-one,
(j) 4-Ethyl-1,3-dihydro-5-[4-[2-(3-methylbutyl)-1H-imidazol-1-yl]benzoyl]-2H-imidazol-2-one,
(k) 4-Ethyl-1,3-dihydro-5-[4-(1H-imidazol-1-yl)benzoyl]-2H-imidazol-2-one,
(l) 1,3-Dihydro-4-[2-(1H-imidazol-1-yl)benzoyl]-5-methyl-2H-imidazol-2-one,
(m) 1,3-Dihydro-4-[3-(1H-imidazol-2-yl)benzoyl]-5-methyl-2H-imidazol-2-one,
(n) 4-Benzoyl-1,3-dihydro-5-methyl-2H-imidazol-2-one,
(o) 4-(4-Fluorobenzoyl)-1,3-dihydro-5-methyl-2H-imidazol-2-one,
(p) 1,3-Dihydro-4-methyl-5-[4-methylthio)benzoyl]-2H-imidazol-2-one.

PROCESS ASPECT

The compounds of this invention can be prepared, in general, by standard techniques analogous to those known in the art. Also provided is a novel synthesis which constitutes the process aspect of this invention whereby are obtained certain of the compounds of this invention as well as compounds known in the art.

Generally, standard techniques which may be employed follow:

Scheme A

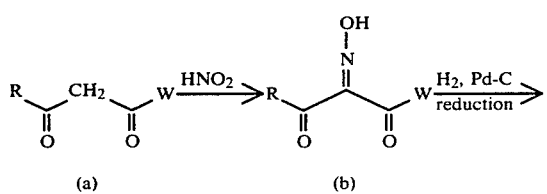

wherein R is as defined in Formula I and W is defined as

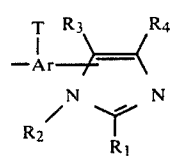

wherein $R_2$ has the same meaning as $R_1$, $R_3$ and $R_4$ previously defined with the proviso that a hydroxyl group is not present alpha to the N atom bearing the $R_2$ group.

In the above Scheme A the diketone (a) starting material may be prepared by a number of known procedures for the synthesis of 1,3-diketones. This diketone is then nitrosated utilizing several known procedures such as treating the diketone in acetic acid with an aqueous solution of sodium or potassium nitrite to produce the requisite oxime (b). The oxime is then reduced via a number of methods such as catalytic reduction in acidic aqueous-organic media, such as hydrochloric acid in methanol over metallic catalysts such as palladium on carbon, or with metals such as zinc in acidic solvents such as acetic acid to produce the aminodiketone (c). The aminodiketone is then reacted with a cyanate salt, preferably sodium or potassium cyanate to produce the imidazolone (d). This latter reaction is performed by mixing the appropriate imidazoleaminodiketone derivative, preferably as an acid addition salt such as the hydrochloride, with about 1 to about 5 molar equivalents of a cyanate salt in a suitable solvent. The reaction is allowed to proceed from about 1 hour to about 5 days depending on the reactants, the solvent and the temperature, which can be from about 0° C. to about 100° C., preferably about 70° C. Suitable solvents for this reaction are any non-reactive solvent such as water or water-miscible solvent such as methanol, acetic acid or tetrahydrofuran, optionally containing up to about 5 molar equivalents, preferably about 1 molar equivalent of a mineral acid such as hydrochloric acid. The preferred solvents are water or aqueous alcohols such as aqueous methanol or aqueous ethanol. The product of this reaction—the desired imidazolonecarbonylarylimidazoles (d) of this invention—may be isolated by procedures standard in the art such as chromatography on silica gel or alumina, conversion to a salt with acid or base followed by neutralization to precipitate the product, or recrystallization as either the neutral product or a salt from a suitable solvent.

Scheme B

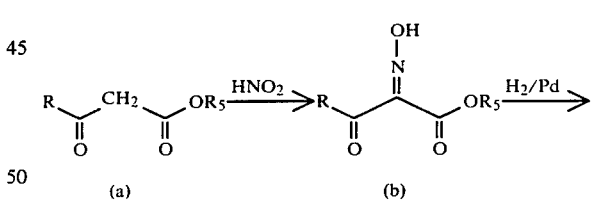

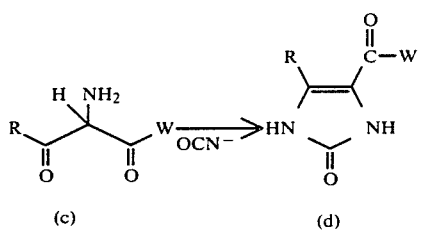

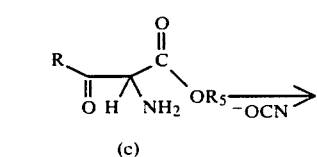

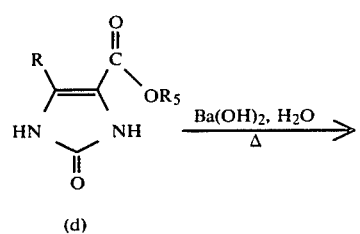

-continued
Scheme B

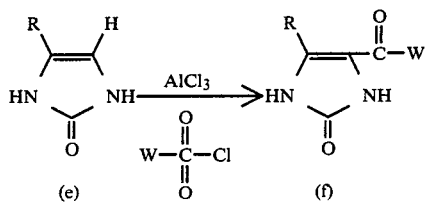

wherein R is as in Formula I, W is as previously defined and $R_5$ is loweralkyl usually methyl or ethyl.

The preceding Scheme B is a more flexible alternative process which employs the synthesis of an appropriate 1,3-dihydro-2H-imidazolone followed by acylation of this intermediate with an acyl halide under Friedel-Crafts conditions. Some of the starting materials (a) are available commercially, others can be synthesized using standard procedures. Compound (d), the 2,3-dihydro-2-oxo-1H-imidazole-4-carboxylic ester, is then hydrolyzed and decarboxylated to the 1,3-dihydro-2H-imidazol-2-one (e). This is then acylated via a conventional Friedel-Crafts procedure with the appropriate acid chloride. The procedure employing aluminum chloride as the catalyst is preferred, thus providing the compound (f).

Scheme C

In yet another process to make certain compounds of the invention an appropriate 1,3-dihydro-4-(halobenzoyl)-2H-imidazol-2-one or 1,3-dihydro-4-(halopyridylcarbonyl)-2H-imidazol-2-one is reacted with the appropriate imidazole wherein halo in a 2-, 4- or 6-halobenzoyl is preferably fluorine and in halopyridine is preferably chlorine or bromine. The reaction is performed by heating the halogen derivative with from about 1 to about 50 molar equivalents, preferably from about 5 to about 20 molar equivalents, of the appropriately substituted imidazole. The reaction is executed using excess appropriately substituted imidazole in a molten state as solvent, or may be performed in a suitable unreactive high boiling solvent such as dimethylsulfoxide or dimethylformamide, optionally in the presence of about 1 molar equivalent of a base such as sodium or potassium carbonate, and when a 3- or 5-halobenzoyl is being utilized, in the presence of a catalytic amount of a cuprous salt. The reaction is allowed to proceed from about 5 hours to about 5 days depending on the reactants, the solvent and the temperature, which may be from about 100° C. to about 200° C., preferably from about 140° C. to about 180° C. The product may be isolated by any of several suitable procedures such as dilution with water or other suitable solvent and filtration of the product, or by distillation or sublimation of the excess appropriately substituted imidazole from the reaction mixture followed by dilution with water or other solvent and filtration. Purification of the product is typically achieved by recrystallization, either as the neutral compound or as an appropriate acid addition salt; by conversion to the corresponding sodium or potassium salt and reprecipitation of the neutral form with carbon dioxide or other weak acid; or by chromatography on silica gel or alumina followed by recrystallization.

The compounds in which one or more of the $R_1$, $R_2$, $R_3$ or $R_4$ loweralkyl substituents are further substituted with one or more hydroxyl groups may be elaborated from the compounds of the invention lacking such substituents by methods known in the art for the preparation of imidazolealkanols. For example, hydroxymethyl groups may be introduced into unsubstituted positions of the imidazole by reaction with aqueous formaldehyde at elevated temperatures, optionally in the presence of acidic or basic catalysts. The hydroxyalkyl substituents may be elaborated from other substituents such as aldehydes and ketones by reduction with metal hydrides such as sodium borohydride. The hydroxyalkyl substituents may be introduced into position $R_2$ by alkylating the compounds wherein $R_2$ is hydrogen with, for example, epoxides or haloalcohols such as trimethylene bromohydrin.

The foregoing described schemes suffer from many problems.

In Scheme A, the indicated starting diketones (a) are usually not commercially available and must therefore be prepared utilizing methods known in the art. The first step shown, nitrosation to give the oximinodiketone, is well known and proceeds smoothly under a variety of conditions known in the art. Step 2, reduction of the oximinodiketone to the aminodiketone, however, is capricious, being subject to overreduction as well as further unwanted side reactions of the product aminodiketone. The final step, reaction of the aminodiketone with cyanate, is also subject to a variety of unwanted side reactions, complicating the purification of the final acyldihydroimidazolone. The entire process suffers from nonconvergence, whereby both the desired R and W groups must be present from the beginning, thus restricting a given process to the manufacture of only a single final product, a serious shortcoming from the point of view of economy.

In Scheme B, the first three steps are analogous to those of Scheme A but are less prone to side reactions than the corresponding steps of Scheme A. The starting materials are commercially available in some cases, or alternatively may be prepared using standard procedures in the art. Step 4, the hydrolysis and decarboxylation of the 2,3-dihydro-2-oxo-1H-imidazole-4-carboxylic ester to the 1,3-dihydro-2H-imidazol-2-one, affords a number of difficulties. Most serious is the difficulty of isolating and purifying the dihydroimidazolones, which are extremely water soluble and nonvolatile. Removal of inorganic ions presents serious problems, unless the metal ion of the base used for the hydrolysis can be quantitatively precipitated from aqueous solution, as is the case when barium hydroxide is used as the base. The use of barium hydroxide, however, leads to variable yields as well as toxicity and waste disposal problems. The final step, Friedel-Crafts acylation of the 1,3-dihydro-2H-imidazole-2-one with the appropriate acid chloride, has been known for many years. A conventional Friedel-Crafts procedure employing aluminum chloride as catalyst is preferred, although a number of other Lewis and Bronsted acid catalysts may be used instead. The most serious problem with this step is in isolation of the products, where inorganic salts, particularly aluminum salts, complicate the separation of the desired, frequently highly insoluble products.

In Scheme C, the halobenzoyl- and halopyridinecarbonylimidazolone starting materials are known compounds (see U.S. Pat. Nos. 4,405,628 and 4,405,635) and may be prepared by methods analogous to those known in the art, i.e. the foregoing Schemes A and B. Most preferably the halobenzoylimidazolones may be prepared by the novel synthesis which constitutes the process aspect of this invention.

The process aspect of the present invention provides a method for the obtention of certain compounds of the present invention in addition to known compounds, which method makes these compounds easily and quickly isolable in excellent purity, while requiring no more steps and employing starting materials and reagents of comparable or lower cost. Overall, the process of this invention affords final products of excellent quality at lower cost.

Particularly, imidazolonecarbonylphenyl derivatives may be expeditiously prepared by the following route.

Scheme D

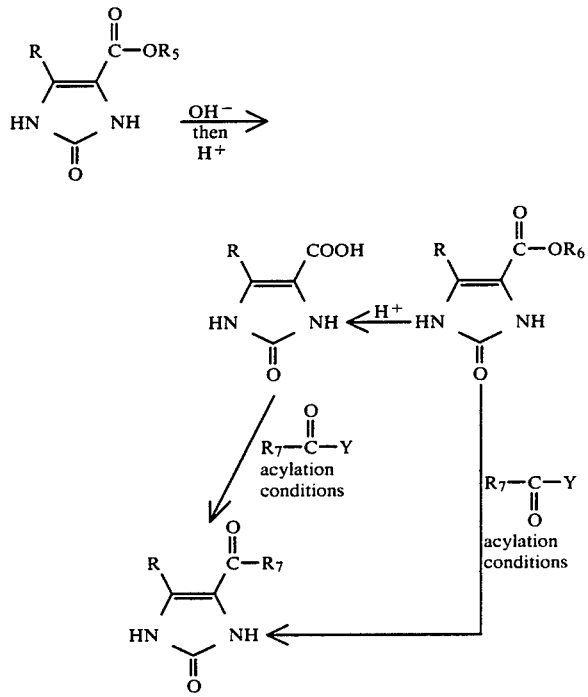

In the foregoing Scheme D, R, $R_5$ are as previously defined, $R_6$ is a tertiary alkyl group such as tertiary butyl, tertiary amyl, and so forth. $R_7$ is the aryl component of acyl groups to be introduced wherein aryl is defined as phenyl, substituted phenyl, wherein the substituents are selected from the group halogen, nitro, loweralkyl, loweralkoxy, loweralkylthio, loweralkylsulfonylamino, loweracylamino or $R_1$, $R_2$, $R_3$ and $R_4$ substituted imidazolyl. Y is hydroxyl, halogen, acyloxy (wherein the acyl component can be either the same acyl group $R_7CO$— as in the desired acyl group to be introduced, or another acyl group with a low tendency to acylate aromatic systems, for example trifluoroacetyl), loweralkoxy, or any other potential leaving group which can generate an acylium ion under acidic conditions. The term "acylation conditions" refers to any reaction conditions capable of generating an electrophilic acylating species such as acylium ion ($R_7$—CO+) from the reagent $R_7$—CO—Y. The term includes reaction conditions of the Friedel-Crafts type, that is, treatment with a Lewis acid catalyst such as a metal halide or a metal in a non-reactive solvent. The metal halides include boron halides, zinc chloride, iron(III) halides, antimony halides, titanium halides, and aluminum halides. The metals are those such as aluminum, iron and zinc. Analogous reactions may also be conducted in the presence of a Bronsted acid catalyst such as sulfuric acid, phosphoric acid, polyphosphoric acid, trifluoroacetic acid. Still further, the reaction may employ reagents combining dehydrating capability with Lewis or Bronsted acidity, such as methanesulfonic acid-phosphorus(V) oxide mixtures, polyphosphate esters, sulfur trioxide-pyridine complex, sulfur trioxide-trialkylamine complexes. Other reaction conditions known to be capable of generating electrophilic acyl species are described in G. Olah, Ed., "Friedel-Crafts and Related Reactions," vol. 3, Interscience, New York, 1964.

When a liquid catalyst is utilized for the acylation it may also be employed in large excess as the reaction solvent. The preferred catalyst is usually polyphosphoric acid, which is then used in large excess as the reaction solvent.

More specifically, a 4-acyl-1,3-dihydro-2H-imidazol-2-one is prepared by the acylation of an appropriate 2,3-dihydro-2-oxo-1H-imidazole-4-carboxylic acid or tertiary alkyl ester thereof, with an appropriate imidazolylbenzoic acid, or a reaction derivative thereof such as the acid chloride. These acylations are performed by mixing the appropriate 2,3-dihydro-2-oxo-1H-imidazole-4-carboxylic acid derivative with about 0.5 to about 5, preferably about 0.5 to about 2 molar equivalents of the appropriate imidazolylbenzoic acid or acid derivative with an excess of a Lewis acid catalyst in a suitable solvent such as nitrobenzene, 1,1,2,2-tetrachloroethane or sulfolane. When the Lewis acid catalyst is a liquid, preferably polyphosphoric acid, it is then utilized both as the catalyst and as solvent in an amount from about 5 times to about 20 times, preferably about 10 times the combined weight of the two reactants. The reaction is allowed to proceed for about 1 hour to about 36 hours, depending on the reactants, solvent, catalyst and temperature, which can be from about 0° C. to about 180° C., preferably from about 70° C. to about 130° C. The product, a 4-acyl-1,3-dihydro-2H-imidazol-2-one, may be isolated by standard techniques known in the art, such as quenching the reaction mixture with ice water, neutralization with base and filtration or extraction of the product. The product is purified by recrystallization, either in its neutral form or as a salt, or by dissolution in acid or base followed by neutralization to precipitate the product, or by chromatography on silica gel or alumina.

Thus, the process of the present invention involves the electrophilic acylation of either a 2,3-dihydro-2-oxo-1H-imidazole-4-carboxylic acid or a tertiary alkyl ester thereof. The carboxylic acids thus employed, as well as the tertiary alkyl esters of these acids, possess only slight solubility in water, facilitating their isolation and purification. When the carboxylic acid is to be used in the process, it can be prepared by basic hydrolysis of a corresponding loweralkyl ester, which compounds are known or may be prepared by methods analogous to those known in the art, specifically by analogy to the first three steps of Scheme B. The hydrolysis is performed by treating the loweralkyl ester with from about 1 to about 3 molar equivalents of an inorganic base, preferably sodium or potassium hydroxide. The reaction is conducted in a non-reactive solvent such as water; an alcohol, such as methanol or ethanol; or a water miscible ether such as tetrahydrofuran. Preferably any nonaqueous solvent is mixed with water. The reaction is allowed to proceed for from about one hour to about 2 days, depending on the reactants, the molar excess of base employed, the solvent and the temperature, which can be from about 0° C. to about 100° C., preferably from about 40° C. to about 80° C. The reaction is allowed to proceed until the starting ester has been consumed, as judged by analysis of the reaction mixture by thin-layer chromatography, gas-liquid partition chromatography, high-pressure liquid chromatography, nuclear magnetic resonance spectrometry or other suitable analytical method. The reaction mixture is then acidified with an aqueous solution of a mineral acid such as hydrochloric or sulfuric acid, and the desired carboxylic acid product collected by filtration, washed thoroughly with water and dried. The carboxylic acid so obtained is generally of excellent purity and suitable for the subsequent acylation without further purification.

Alternatively, the 2,3-dihydro-2-oxo-1H-imidazole-4-carboxylic acid intermediates may be prepared by acid catalyzed cleavage of a corresponding tertiary alkyl ester. These tertiary alkyl esters are known compounds or can be prepared using methods analogous to those known in the art, specifically by analogy to the first three steps of Scheme B. The cleavage of the tertiary alkyl ester is performed by treating the ester with from about 0.01 molar equivalents to about 100 molar equivalents of a strong acid in a suitable solvent. The strong acid can be a halogenated carboxylic acid such as trifluoroacetic acid; a sulfonic acid such as methanesulfonic acid or toluenesulfonic acid; or a mineral acid such as sulfuric acid, hydrochloric acid or phosphoric acid. Suitable solvents include any non-reactive solvents such as water; aliphatic hydrocarbons such as hexane, petroleum ether and the like; aromatic solvents such as benzene, toluene and xylene; and halogenated solvents such as dichloromethane, chloroform, carbon tetrachloride, dichloroethane, chlorobenzene, ortho-dichlorobenzene and FREONS. When the acid catalyst is itself liquid it may be used in excess as solvent. The reaction is allowed to proceed for from about 5 minutes to about 2 days depending on the reactant, nature and amount of acid catalyst, solvent and temperature, which can be from about 0° C. to about 100° C., preferably about 25° C. The preferred reaction conditions employ from about 5 molar equivalents to about 10 molar equivalents of trifluoroacetic acid both as catalyst and solvent, whereby the reaction is complete within about 5 minutes at about 25° C. The carboxylic acid product is isolated by standard techniques well known in the art, such as filtration; dilution with water and filtration; and evaporation or distillation of solvent under reduced pressure followed by filtration. The crude product, which may have variable amounts of the acid catalyst more or less strongly complexed with it, is purified by thorough washing with water followed by drying. The 2,3-dihydro-2-oxo-1H-imidazole-4-carboxylic acid so obtained is usually of excellent purity and can be used in the subsequent acylation without further purification.

METHOD-OF-USE AND PHARMACEUTICAL COMPOSITION ASPECT

The imidazolonecarbonylarylimidazoles of this invention and their pharmaceutically acceptable salts as disclosed in general Formula I may be used for the treatment of congestive heart failure, including both acute and chronic heart failure, and involving either or both of the left and right heart ventricles.

Additionally, they may be used in the treatment of any other condition which requires the strengthening of heart action with a cardiotonic. Whilst certain of the compounds of Formula I also have been found to have antiarrhythmic activity, others would be expected to have other medically useful properties such as antithrombotic, platelet aggregation inhibition, antihypertensive, and bronchodilator actions.

Most generally, however, the compounds of this invention find their usefulness as cardiotonic agents. Their utility as cardiotonic agents may be determined in isolated cat or ferret papillary muscle, using standard isometric recording techniques, and by administering the compound (0.03–10 mg/kg) to be tested intravenously, orally, or intraduodenally in a suitable vehicle, to dogs which have been anesthetized and instrumented for routine hemodynamic recordings, including the establishment of arterial and venous lines, the introduction of a left ventricular catheter for the measurement of left ventricular pressure and its first derivative (dp/dt), and suitable blood flow probes to determine aortic and coronary blood flow. Acute heart failure can be induced by sequential ligation of branches of the left coronary arteries, until left ventricular end diastolic pressure exceeds 15 mm Hg.

In general the compounds of this invention may be administered orally or parenterally. The dosage administered will be dependent on the mammalian host being treated, the route of administration and the magnitude and type of cardiotonic effect to be elicited.

For oral or parenteral administration the effective cardiotonic dose of the compounds of this invention, for example, 1,3-dihydro-4-methyl-5-[4-(2-methyl-1H-imidazol-1-yl)benzoyl]-2H-imidazol-2-one or 1,3-dihydro-4-[4-(1H-imidazol-1-yl)benzoyl]-5-methyl-2H-imidazol-2-one ranges from about 0.001 mg/kg of body weight to about 30 mg/kg of body weight. Repetitive dosing may be required to achieve the appropriate positive inotropic effect for 24 hours.

For oral administration the compound to be administered can be formulated by admixing with any number of suitable pharmaceutical diluents and carriers such as lactose, sucrose, starch powder, cellulose, calcium sulfate, sodium benzoate, and the like. Such formulations can be compressed into tablets or encapsulated into gelatin capsules for conventional oral administration.

For parenteral administration a compound of this invention can be formulated, for example, for intramuscular or intravenous administration. Such parenteral administration formulations can be accomplished with any of a number of pharmaceutically acceptable carriers and diluents to constitute an injectable liquid solution. Commonly used diluents and carriers include water or saline solutions, buffered aqueous solutions, including dispersing and surface active agents if necessary.

Thus, there is provided by this invention a method of eliciting a cardiotonic effect in a mammalian host having a disease condition in which therapeutic benefit is derived from elicitation of a cardiotonic effect which comprises administering to said host a non-toxic cardiotonically effect amount of the compounds of this invention.

The invention described hereinabove is illustrated below in the Preparations and Examples, which, however, is not to be construed as limiting the scope of this invention.

PREPARATIONS

Preparation 1

Methyl 4-(1H-imidazol-1-yl)benzoate and free acid

Combine methyl 4-fluorobenzoate (1.52 g, 10 mmol), 1H-imidazole (0.82 g, 12 mmol) and potassium carbonate (1.40 g, 10 mmol) in dimethylsulfoxide (7 mL) and heat the mixture with stirring at 120°–130° C. for 5 hours, cool, add water and acid, extract with ether. Adjust the pH of the aqueous layer to 8 with sodium carbonate, extract with ether, dry the extract with sodium sulfate and evaporate. 4-(1H-Imidazol-1-yl)benzoic acid is prepared by refluxing this methyl ester (0.61 g, 3 mmol) in 5 mL of 10% aqueous sodium hydroxide for five minutes; cool, neutralize to pH 6–7 with hydrochloric acid, filter and dry the precipitated acid.

Preparation 2

2,3-Dihydro-5-methyl-2-oxo-1H-imidazole-4-carboxylic acid 2,3-Dihydro-5-methyl-2-oxo-1H-imidazole-4-carboxylic acid 1,1-dimethylethyl ester (110.1 g, 0.556 mol) is added in portions to stirred trifluoroacetic acid (500 g). After stirring the resulting mixture at room temperature for 20 minutes the suspension is evaporated in vacuo. The solid residue is mixed with water (700 mL), the mixture filtered, and the solid residue washed with an additional portion of water (700 mL). The filter cake is then dried for 1.5 hr. at ca. 105° C., then overnight at room temperature to produce the title compound.

Preparation 3

5-Ethyl-2,3-dihydro-2-oxo-1H-imidazole-4-carboxylic acid

Following the procedure of Preparation 2, but substituting 5-ethyl-2,3-dihydro-2-oxo-1H-imidazole-4-carboxylic acid 1,1-dimethylethyl ester for 2,3-dihydro-5-methyl-2-oxo-1H-imidazole-4-carboxylic acid 1,1-dimethylethyl ester results in the title compound.

EXAMPLES

Example I

A.
1,3-Dihydro-4-[4-(1H-imidazol-1-yl)benzoyl]-5-methyl-2H-imidazol-2-one hydrochloride 2,3-Dihydro-5-methyl-2-oxo-1H-imidazole-4-carboxylic acid (0.77 g, 4 mmol) and 4-(1H-imidazol-1-yl)benzoic acid (0.38 g, 2 mmol) are mixed with polyphosphoric acid (6.2 g) and the mixture rapidly heated to 80° C. with stirring. With continued stirring, the mixture is heated to 120° C. for 24 hr. The reaction mixture is cooled, mixed with ice (25 g) and the resulting mixture neutralized to pH 7–8 by the addition of solid potassium hydroxide with cooling and stirring. The suspension is filtered to afford the free base form of the title compound. This solid is mixed with water (5 mL) and 1M hydrochloric acid (3 mL), the mixture heated, treated with charcoal, filtered and cooled. The crystals are collected by filtration, washed with water and methanol and dried to give the title compound.

NMR (DMSO-d$_6$): δ=1.89(s,3), 7.62(t,1), 7.81(d,2), 7.88(d,2), 8.17(t,1), 9.22(t,1), 10.38(br s, 1) and 10.98(br s, 1)ppm; solvent at 2.50 ppm and H$_2$O at 3.45 ppm.

B.
4-Ethyl-1,3-dihydro-5-[4-(1H-imidazol-1-yl)benzoyl]-2H-imidazol-2-one In a manner similar to that described in Example IA react 5-ethyl-2,3-dihydro-2-oxo-1H-imidazole-4-carboxylic acid and 4-(1H-imidazol-1-yl)benzoic acid, dissolve the crude free base in aqueous sodium hydroxide and reprecipitate with carbon dioxide to produce the title compound.

NMR (DMSO-d$_6$): δ=1.04(t,3), 2.25(quar,2), 7.19(s,1), 7.79(dd,2), 7.84(dd,2), 7.88(s,1), 8.41(s,1), 10.34(br s,1) and 10.98(br s,1) ppm.

Example II

In a manner similar to that described in Example I react 2,3-dihydro-5-methyl-2-oxo-1H-imidazole-4-carboxylic acid with the following reactants respectively:
(a) 4-(2-methyl-1H-imidazol-1-yl)benzoic acid,
(b) 4-(1H-imidazol-2-yl)benzoic acid,
to produce the following final products respectively:
(c) 1,3-dihydro-4-methyl-5-[4-(2-methyl-1H-imidazol-1-yl)-benzoyl]-2H-one hydrochloride hydrate, NMR (D$_2$O): δ=2.01(s,3), 2.62(s,3), 7.52(s,1), 7.61(s,1), 7.72(d,2), 7.92(d,2) ppm; solvent at 4.80 ppm.
(d) 1,3-dihydro-4-[1H-imidazol-2-yl)benzoyl]-5-methyl-2H-imidazol-2-one NMR (DMSO-d$_6$): δ=1.89(s,3), 7.09(s,1), 7.32(s,1), 7.68(d,2), 8.03(d,2), 10.32(s,1), 10.88(s,1), and 12.71(s,1) ppm; solvent at 2.52 ppm and H$_2$O at 3.34 ppm.

Example III

4-Ethyl-1,3-dihydro-5-[4-[2-(3-methylbutyl)imidazol-1yl]benzoyl]-2H-imidazol-2-one In a manner similar to that described in Example I react 4-[2-(3-methylbutyl)-1H-imidazol-1-yl]benzoic acid and 5-ethyl-2,3-dihydro-2-oxo-1H-imidazole-4-carboxylic acid to produce the title compound which can be purified by chromatography of the crude base on silica gel.

NMR (DMSO-d$_6$): δ=0.75(d,6), 1.02(t,3), 1.43(m,3), 2.22(quar,2), 2.68(t,2), 7.00(s,1), 7.35(s,1), 7.58(d,2), 7.68(d,2), 11.02(br s,1) and 11.40(br s,1) ppm.

Example IV

1,3-Dihydro-4-methyl-5-[4-(4-methyl-1H-imidazol-1-yl)benzoyl]-2H-imidazol-2-one 4-(4-Fluorobenzoyl)-1,3-dihydro-5-methyl-2H-imidazol-2-one (6.6 g, 30 mmol) is combined with 4-methyl-1H-imidazole (33 g, ca. 400 mmol) in a sealed flask and the mixture heated with stirring at ca. 140° C. overnight. The mixture is cooled, water (120 mL) added and the mixture stirred in an ice bath. The suspension is filtered and the filter cake washed with water and acetone. The solid is heated under reflux in a mixture of 2-propanol (300 mL) and water (200 mL) until dissolution is complete. The solution is filtered, reheated to dissolve some precipitated solid and allowed to cool slowly to room temperature. After 2.5 days the mixture is cooled in ice for 2 hr, the solid collected by filtration, washed with acetone, and dried in vacuo at 105° C. for 23 hr to produce the title compound.

NMR (DMSO-d$_6$): δ=1.91(s,3), 2.18(s,3), 7.58(s,1), 7.74(s,4), 8.29(s,1), 10.33(s,1), 10.92(s,1); solvent at 2.50 ppm and H$_2$O at 3.32 ppm.

Example V

A.
1,3-Dihydro-4-methyl-5-[4-(2,4,5-trimethyl-1H-imidazol-1-yl)benzoyl]-2H-imidazol-2-one In a manner similar to Example IV react 4-(4-fluorobenzoyl)-1,3-dihydro-5-methyl-2H-imidazol-2-one with 2,4,5-trimethyl-1H-imidazole to produce the title compound.

NMR (DMSO-d$_6$): $\delta$=1.85(s,3), 1.90(s,3), 2.05(s,3), 2.10(s,3), 7.44(d,2), 7.74(d,2), 10.44(br s,1) and 10.98(br s,1) ppm.

B.
1,3-Dihydro-[4-[2-(1H-imidazol-1-yl)pyridin-4-yl]carbonyl]-5-methyl-2H-imidazol-2-one In a manner similar to Example IV react 4-[(2-chloropyridin-4-yl)carbonyl]-1,3-dihydro-5-methyl-2H-imidazol-2-one with 1H-imidazole to produce the title compound.

NMR(DMSO-d$_6$): $\delta$=1.90(s,3), 7.14(s,1), 7.47(d,1), 7.98(s,1), 8.05(s,1), 8.61(d,1), and 8.62(s,1) ppm; solvent at 2.50 ppm and H$_2$O at 3.32 ppm.

Example VI

4-[4-(1H-Benzimidazol-1-yl)benzoyl]-1,3-dihydro-5-methyl-2H-imidazol-2-one 1,3-Dihydro-4-(4-fluorobenzoyl)-5-methyl-2H-imidazol-2-one (4.4 g, 20 mmol) is combined with 1H-benzimidazole (30 g, 254 mmol) in a sealed flask with stirring, and the mixture heated at about 185° C. for about 7 hr. The mixture is cooled, 120 mL of methanol is added and the mixture stirred in an ice bath. The suspension is filtered and the filter cake washed with water and acetone. The remainder of the process is carried out as in Example IV to yield the title compound.

NMR (DMSO-d$_6$): $\delta$=1.96(s,1), 7.38(m,2), 7.82(m,6), 8.67(s,1), 10.37(s,1), 10.95(s,1)ppm; solvent at 2.5 ppm and H$_2$O at 3.32 ppm.

Example VII

1,3-Dihydro-4-[4-[2-(hydroxymethyl)-1H-imidazol-1-yl]benzoyl]-5-methyl-2H-imidazol-2-one 1,3-Dihydro-4-[4-(1H-imidazol-1-yl)benzoyl]-5-methyl-2H-imidazol-2-one (5.85 g, 21.8 mmol) (Example I) is combined in a pressure tube containing a magnetic stir bar with 37% aqueous formaldehyde (300 mL) and the mixture heated with stirring at 120° C. for 18 hr. The mixture is cooled, the tube opened and the solution evaporated in vacuo. Chromatography of the residue on silica gel affords the title compound.

NMR (DMSO-d$_6$): $\delta$=1.91(s,3), 4.44(d,2), 5.50(t,1), 7.05(s,1), 7.50(s,1), 7.74(m,4), 10.40(s,1), 10.98(s,1) ppm; solvent at 2.52 ppm and H$_2$O at 3.38 ppm.

Example VIII

4-(4-Fluorobenzoyl)-1,3-dihydro-5-methyl-2H-imidazol-2-one 2,3-Dihydro-5-methyl-2-oxo-1H-imidazole-4-carboxylic acid (71.0 g, 0.5 mol) and 4-fluorobenzoic acid (105 g, 0.75 mol) are mixed together then covered with polyphosphoric acid (1.6 Kg). The mixture is rapidly heated to 60° C. with stirring, then gradually heated to 110° C. over 2.5 hr. with continued stirring. After stirring at ca. 110° C. for an additional 2 hr. the mixture is cooled to 60° C. and mixed with crushed ice (3.5 Kg).

After all the ice has melted, the mixture is filtered and the solid washed with water. The filter cake is suspended in water (800 mL) and the pH raised to approximately 8 by the gradual addition of 10% aqueous sodium hydroxide solution, and the mixture stirred overnight. The pH is adjusted to 8–9, the solid collected by filtration, washed thoroughly with water and dried. Recrystallization from isopropanol-water affords the title compound.

NMR (DMSO-d$_6$): $\delta$=1.86(s,3), 7.33(t,2) and 7.68(m,2)ppm; solvent at 2.5 ppm and H$_2$O at 3.4 ppm.

Example IX

In a manner similar to Example VIII react 2,3-dihydro-5-methyl-2-oxo-1H-imidazole-4-carboxylic acid with the following compounds respectively:
(a) benzoic acid,
(b) 4-(methylthio)benzoic acid,
to produce the following compounds respectively:
(c) 4-benzoyl-1,3-dihydro-5-methyl-2H-imidazol-2-one,
(d) 1,3-Dihydro-4-methyl-5-[4-(methylthio)benzoyl]-2H-imidazol-2-one.

Example X

4-Ethyl-1,3-dihydro-5-[4-(2-methyl-1H-imidazol-1-yl)benzoyl]-2H-imidazol-2-one In a manner similar to Example I react 2,3-dihydro-5-ethyl-2-oxo-1H-imidazole-4-carboxylic acid with 4-(2-methyl-1H-imidazol-1-yl)benzoic acid to produce the title compound.

NMR (DMSO-d$_6$): $\delta$=1.02(t,3), 2.25(quar,2), 2.26(s,3), 6.95(s,1), 7.37(s,1), 7.56(d,2), 7.75(d,2), 10.40(br s,1), and 11.04(br s,1) ppm.

We claim:
1. A compound of the formula:

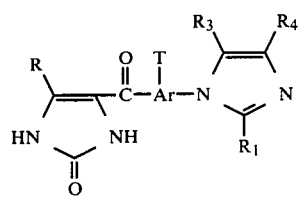

wherein
R is hydrogen or lower alkyl;
Ar is phenyl or pyridyl;
T is hydrogen, hydroxy, halogen or lower alkyl;
R$_1$, R$_3$ and R$_4$ are hydrogen or lower alkyl optionally substituted by 0 to 2 hydroxyl groups, or R$_3$ and R$_4$ taken together form a benzene ring;
with the provisos that:
(a) when T is hydroxy, Ar is phenyl,
(b) when one of R$_1$, R$_3$ and R$_4$ is lower alkyl substituted with 2 hydroxyl groups both hydroxyls cannot be on the same carbon atom;
or a pharmaceutically acceptable salt thereof.

2. A compound of claim 1 wherein Ar is phenyl.
3. A compound of claim 1 wherein R is loweralkyl.
4. A compound of claim 1 wherein T is hydrogen.
5. A compound of claim 1 wherein Ar is phenyl, R is loweralkyl and T is hydrogen.
6. A compound of claim 5 of the following formula:

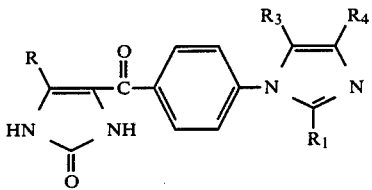

wherein
R is lower alkyl and
R$_1$, R$_3$ and R$_4$ are hydrogen, loweralkyl optionally substituted by 0 to 2 hydroxyl groups, or R$_3$ and R$_4$ can be taken together to form a benzene ring, with the proviso that: when said second lower alkyl has 2 hydroxyl groups both cannot be on the same carbon atom.

7. A compound of claim 6 wherein R is methyl or ethyl, R$_1$, R$_3$ and R$_4$ are hydrogen or loweralkyl with no hydroxyl substituents.

8. A compound of claim 1 which is 1,3-dihydro-4-[[2-(1H-imidazol-1-yl)pyridin-4-yl]carbonyl]-5-methyl-2H-imidazol-2-one.

9. A compound of claim 6 which is 4-[4-(1H-benzimidazol-1-yl)benzoyl]-1,3-dihydro-5-methyl-2H-imidazol-2-one.

10. A compound of claim 6 which is 1,3-dihydro-4-[4-(2-hydroxymethyl-1H-imidazol-1-yl)benzoyl]-5-methyl-2H-imidazol-2-one.

11. A compound of claim 7 which is 1,3-dihydro-4-methyl-5-[4-(2-methyl-1H-imidazol-1-yl)benzoyl]-2H-imidazol-2-one.

12. A compound of claim 7 which is 1,3-dihydro-4-(1H-imidazol-1-yl)benzoyl]-5-methyl-2H-imidazol-2-one.

13. A compound of claim 7 which is 1,3-dihydro-4-methyl-5-[4-(4-methyl-1H-imidazol-1-yl)benzoyl]-2H-imidazol-2-one.

14. A compound of claim 7 which is 1,3-dihydro-4-methyl-5-[4-(2,4,5-trimethyl-1H-imidazol-1-yl)benzoyl]-2H-imidazol-2-one.

15. A compound of claim 7 which is 4-ethyl-1,3-dihydro-5-[4-(2-methyl-1H-imidazol-1-yl)benzoyl]-2H-imidazol-2-one.

16. A compound of claim 7 which is 4-ethyl-1,3-dihydro-5-[4-[2-(3-methylbutyl)-1H-imidazol-1-yl]benzoyl]-2H-imidazol-2-one.

17. A compound of claim 7 which is 4-ethyl-1,3-dihydro-5-[4-(1H-imidazol-1-yl)benzoyl]-2H-imidazol-2-one.

18. A pharmaceutical composition for treating cardiac failure comprising a non-toxic cardiotonically effective amount of a compound of claim 1 in admixture with a non-toxic pharmaceutically acceptable carrier.

19. The method of treating cardiac failure in a mammalian host having a disease condition in which therapeutic benefit is derived from elicitation of a cardiotonic effect which comprises administering to said host a non-toxic cardiotonically effective amount of a compound of claim 1.

* * * * *